US008057533B2

(12) United States Patent
Mangin et al.

(10) Patent No.: US 8,057,533 B2
(45) Date of Patent: Nov. 15, 2011

(54) APPARATUS WITH VISUAL MARKER FOR GUIDING DEPLOYMENT OF IMPLANTABLE PROSTHESIS

(75) Inventors: Stephen P. Mangin, Ashland, MA (US); Peter J. Shank, Boylston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/696,845

(22) Filed: Oct. 29, 2003

(65) Prior Publication Data

US 2005/0096721 A1    May 5, 2005

(51) Int. Cl.
*A61F 2/84* (2006.01)
(52) U.S. Cl. ............ 623/1.34; 623/1.32; 623/1.12
(58) Field of Classification Search ............ 623/1.12, 623/1.34, 1.2
See application file for complete search history.

(56) References Cited

U.S. PATENT DOCUMENTS

| | | | |
|---|---|---|---|
| 5,160,341 A | 11/1992 | Brenneman et al. | |
| 5,401,257 A * | 3/1995 | Chevalier et al. | 604/265 |
| 5,405,378 A | 4/1995 | Strecker | |
| 5,480,423 A * | 1/1996 | Ravenscroft et al. | 623/1.11 |
| 5,653,748 A * | 8/1997 | Strecker | 623/1.11 |
| 5,662,713 A | 9/1997 | Andersen et al. | |
| 5,702,418 A | 12/1997 | Ravenscroft | |
| 5,792,144 A * | 8/1998 | Fischell et al. | 606/108 |
| 5,855,615 A | 1/1999 | Bley et al. | |
| 5,968,052 A | 10/1999 | Sullivan, III et al. | |
| 6,335,028 B1 | 1/2002 | Vogel et al. | |
| 2002/0087186 A1 | 7/2002 | Shelso | |
| 2003/0121148 A1 * | 7/2003 | DiCaprio | 29/890.09 |

OTHER PUBLICATIONS

Boston Scientific, *Ultraflex Esophageal Stent System, The Total Approach to Esophagel Stenting*, Brochure, 1998, 6 pages.
Communication pursuant to Article 94(3) EPC, European Patent Office, European Patent Application No. 04 784 786.8-2310, Jun. 23, 2008 (3 pages).
Communication, Supplementary European Search Report, European Patent Office, European Patent Application No. 04 784 786.8-2310, Mar. 6, 2008 (3 pages).
PCT International Preliminary Report on Patentability for International Application No. PCT/US2004/031074, May 1, 2006 (4 pages).
PCT International Search Report for International Application No. PCT/US2004/31074, Dec. 20, 2005 (1 page).

* cited by examiner

*Primary Examiner* — Thomas J Sweet
*Assistant Examiner* — Christopher D Prone
(74) *Attorney, Agent, or Firm* — Vidas, Arrett & Steinkraus

(57) ABSTRACT

An apparatus for use by an operator in a cavity of a mammalian body with a scope having a distal face providing a field of view. The apparatus includes a flexible elongate member having a distal extremity adapted for extending into the cavity and a proximal extremity accessible from outside of the mammalian body when the distal extremity is disposed in the cavity. An expandable prosthesis is releaseably secured to the distal extremity of the flexible elongate member. A visual marker capable of being seen by the operator in the field of view is secured to one of the distal extremity of the flexible elongate member and the prosthesis for facilitating placement of the prosthesis in the mammalian body.

21 Claims, 4 Drawing Sheets

US 8,057,533 B2

APPARATUS WITH VISUAL MARKER FOR GUIDING DEPLOYMENT OF IMPLANTABLE PROSTHESIS

SCOPE OF THE INVENTION

The present invention relates to apparatus for deploying implantable prostheses within mammalian bodies and more particularly to apparatus for deploying stents within human bodies.

BACKGROUND

Delivery systems have been provided for the deployment of stents and other prostheses. Such delivery systems, for example, have been used for the percutaneous implantation of vascular prostheses. See in this regard U.S. Pat. No. 5,653,748 issued Aug. 5, 1997, the entire content of which is incorporated herein by this reference. Delivery systems have also been provided for esophageal stenting. See in this regard Ultraflex™ Esophageal Stent System, The Total Approach to Esophageal Stenting, copyrighted in 1998 by Boston Scientific Corporation, the entire content of which is incorporated herein by this reference (the "Ultraflex Article").

Endoscopically placed stents are often delivered with the aid of fluoroscopy. For example, radiopaque markers can be affixed to the delivery system or the stent itself and aligned with external radiopaque markers placed on the body of the patient. Unfortunately, fluoroscopically aided delivery systems can undesirably expose the patient and the operating physician to x-rays. In addition, such systems require the use of expensive equipment that can require further expense to set up for a procedure. It would thus be desirable to provide a delivery system which overcomes these disadvantages.

Stents have previously been encased in colored gelatin to bind the stent to the delivery system in place of a crocheted suture or other stent securement means.

SUMMARY OF THE INVENTION

The present invention provides an apparatus for use by an operator in a cavity of a mammalian body with a scope having a distal face providing a field of view. The apparatus includes a flexible elongate member having a distal extremity adapted for extending into the cavity and a proximal extremity accessible from outside of the mammalian body when the distal extremity is disposed in the cavity. An expandable prosthesis and means for releaseably securing the prosthesis to the distal extremity of the flexible elongate member are provided. A visual marker capable of being seen by the operator in the field of view is secured to one of the distal extremity of the flexible elongate member and the prosthesis for facilitating placement of the prosthesis in the mammalian body.

BRIEF DESCRIPTION OF THE DRAWINGS

The accompanying drawings, which are somewhat schematic in some instances and are incorporated in and form a part of this specification, illustrate several embodiments of the invention and, together with the description, serve to explain the principles of the invention.

DESCRIPTION OF THE INVENTION

Figures 1, 2:
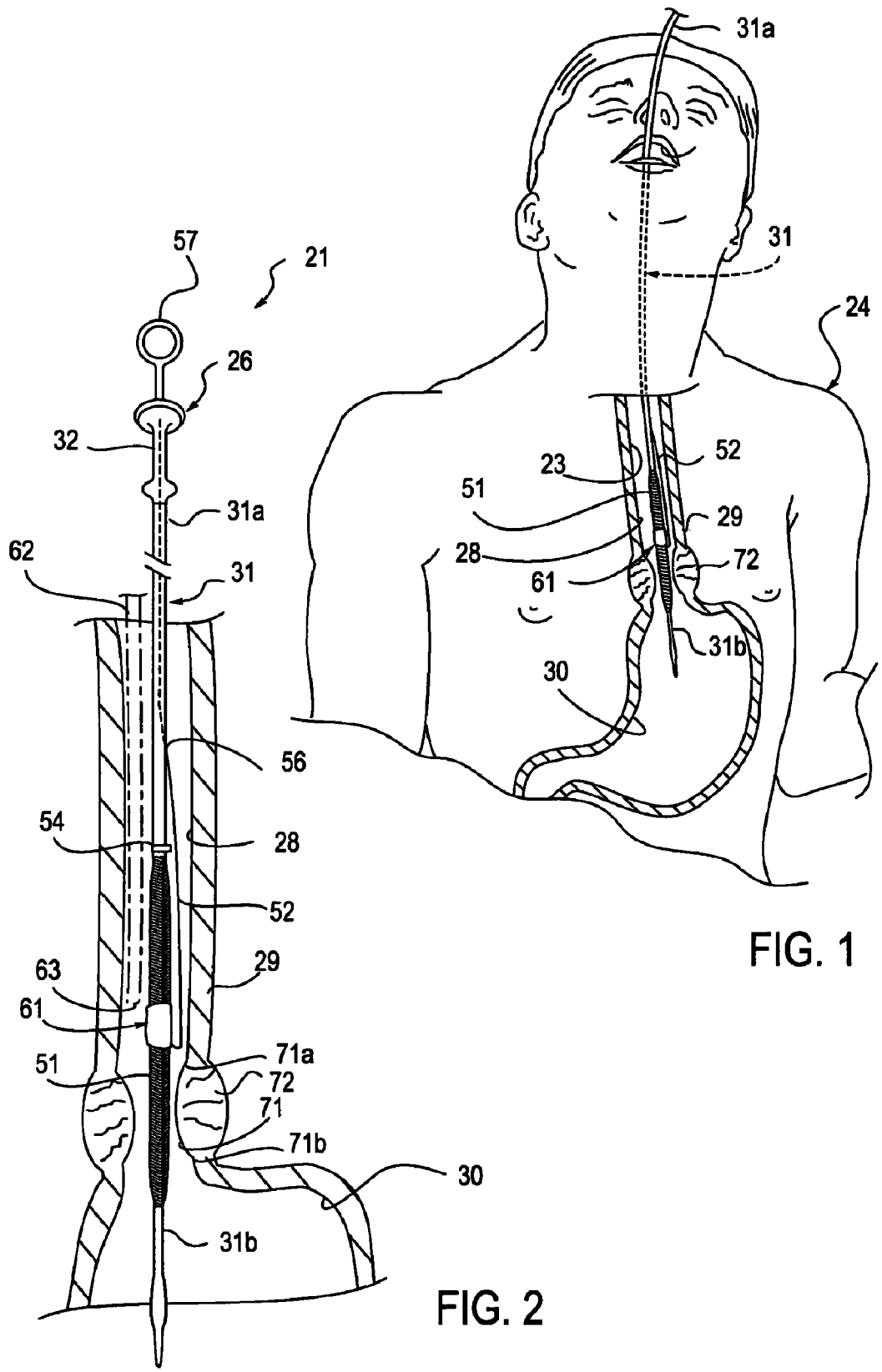
FIG. 1 is an elevational view of an apparatus for guiding deployment of an implantable prosthesis of the present invention in a first position in a passageway of a patient.
FIG. 2 is an enlarged elevational view of the apparatus of FIG. 1 in the first position in a portion of the passageway of the patient.
Figure 3:
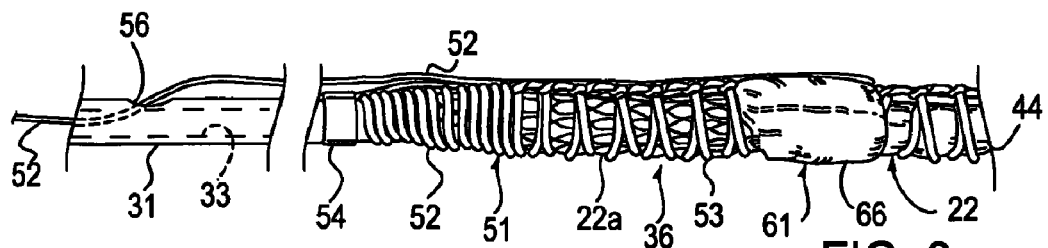
FIG. 3 is a side elevational view of a portion of the apparatus of FIG. 1 in the first position.

In general, apparatus 21 of the present invention is for use in deploying a prosthesis 22 in a cavity 23 of a mammalian body 24 (see FIGS. 1-3). The apparatus 21 includes an elongate device 26 and the prosthesis 22 is mounted on a distal portion of the device 26. In one preferred embodiment, the body 24 is a human body and cavity 23 is any suitable lumen, passage or passageway in the body, for example the gastrointestinal tract 23 extending from the mouth 27 to the anus (not shown). A portion of the gastrointestinal tract is shown in FIG. 1 and includes the esophagus 28, formed by a tubular wall 29, and the stomach 30.

Device 26 can be of the type described in the Ultraflex Article. In general, device 26 comprises a flexible elongate member or shaft 31 having a proximal extremity 31a and a distal extremity 31b (see FIG. 2). A handle 32 is formed on proximal extremity 31a and the shaft 31 is provided with at least one lumen or passageway 33 extending from the proximal extremity 31a to the distal extremity 31b thereof.

Figure 5:
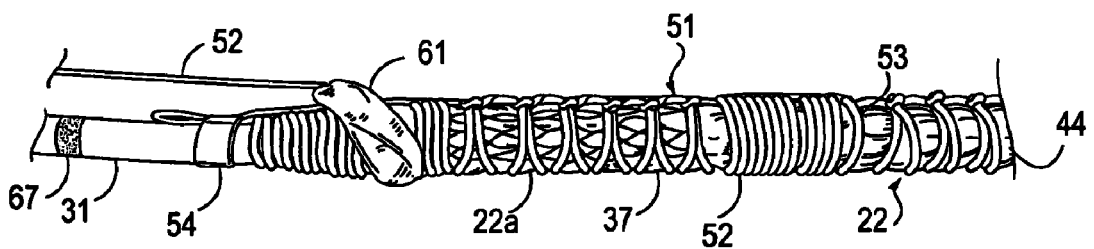
FIG. 5 is a side elevational view of a portion of the apparatus of FIG. 1 in a third position.
Figure 6:
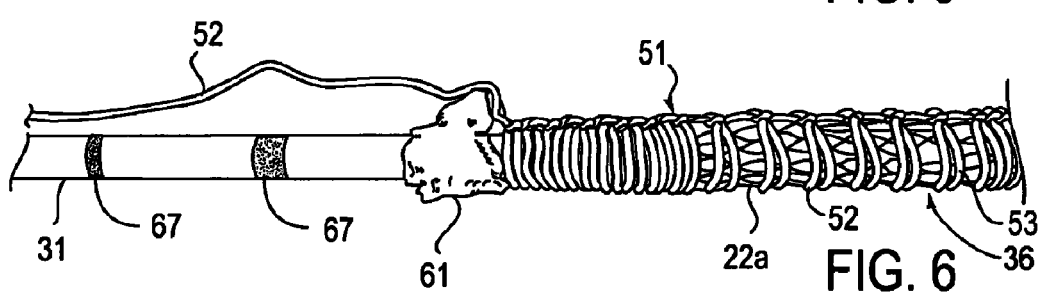
FIG. 6 is a side elevational view of a portion of the apparatus of FIG. 1 in a fourth position.
Figure 7:
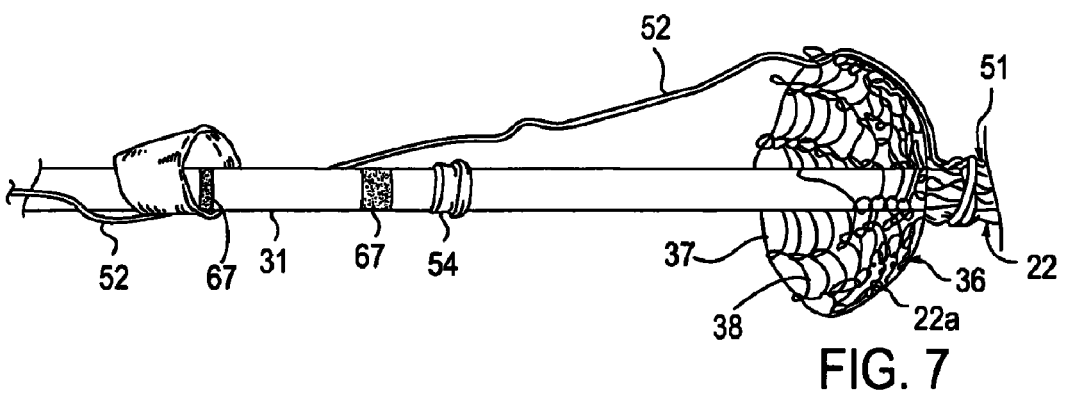
FIG. 7 is a side elevational view of a portion of the apparatus of FIG. 1 in a fifth position.
Figure 9:
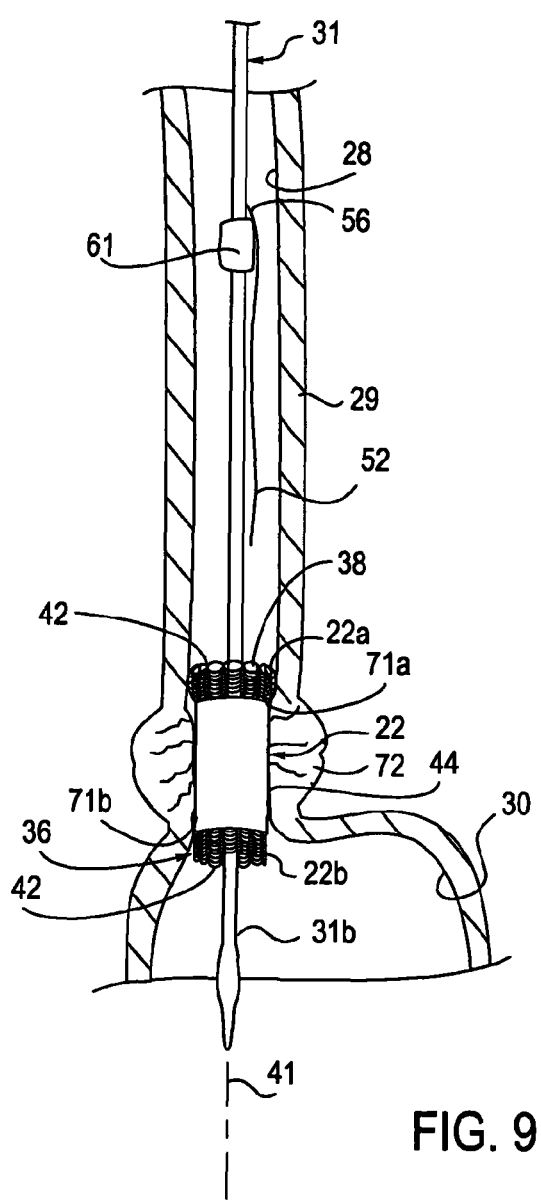
FIG. 9 is an enlarged elevational view, similar to FIG. 2, of the apparatus of FIG. 1 in a sixth position in the passageway of the patient.

A stent 22 or other suitable prosthesis is removably mounted on distal extremity 31b of shaft 31 (see FIGS. 3-9). Stent 22 can be of the type disclosed in U.S. Pat. No. 5,662,713 issued Sep. 3, 1997, the entire content of which is incorporated herein by this reference. In general, stent 22 includes at least one mesh 36 formed from at least one wire 37 made from metal or any other suitable material and having a length ranging from six to 15 centimeters. The wire 37 is preferably made from a shape memory alloy such as Nitinol. As illustrated in FIG. 7, wire 37 is knitted into a plurality of overlapping loops 38. The elongate stent 22 extends along a longitudinal axis 41 and has a first or proximal end portion 22a and a second or distal end portion 22b, one or both of which can be flared, and corresponding first and second ends 42,43. The stent can optionally include a membrane 44 extending around at least a portion of the length of the wire mesh 36 and preferably between the proximal and distal end portions 22a and 22b of the stent. Membrane 44 can be a semi-permeable compliant membrane made from any suitable material such as expanded polytetrafluoroethylene (teflon), latex or silicone and preferably silicone. Stent 22, as shown in FIG. 9, has a proximal end portion 22a which is flared, a distal end portion which is not flared and a membrane 44 extending therebetween.

Figure 4:
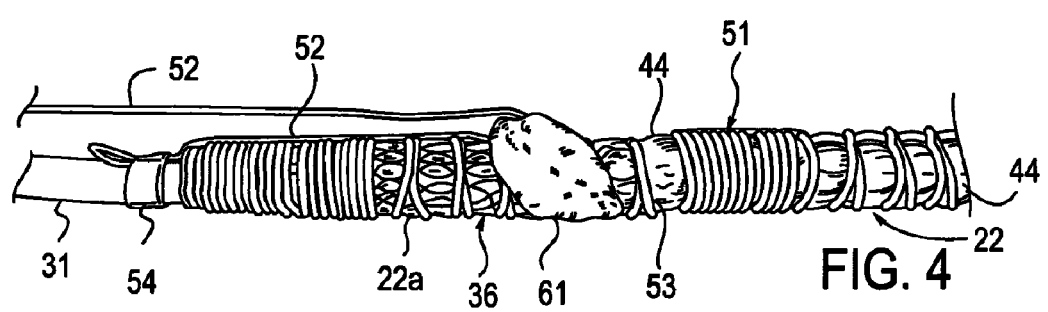
FIG. 4 is a side elevational view of a portion of the apparatus of FIG. 1 in a second position.

Means is included within apparatus 21 for releaseably securing prosthesis 22 to distal extremity 31b of device 26. One preferred means is a mesh 51 extending along at least a portion of the length of the prosthesis 22 (see FIGS. 2-3). The mesh 51 is preferably formed of a crocheted material such as of the type disclosed in U.S. Pat. No. 5,653,748. In this regard, mesh 51 can be formed from a thread 52 having a plurality of loops 53 extending around the prosthesis. The thread 52 is preferably black in color and is secured to shaft 31 at one end of the mesh 51 by any suitable means such as a flexible band 54 made from an elastomeric or other suitable material (see FIGS. 3-5). Band 54 is shown in FIGS. 3-5 as being located adjacent the proximal end portion 22a of the stent, the end at which release of the stent from device 26 commences. Threaded mesh 51 preferably extends along the entire length of the stent 22 and more preferably beyond each of the ends. 42 and 43 of the stent 22, as illustrated in FIG. 3 with respect to the proximal end of the stent. One end of the thread 52 extends proximally of stent 22 along the outside of shaft 31 before passing through an opening, porthole or skive 56 provided in the side of shaft 31 and communicating with an internal passage, such as passage 33, extending to proximal extremity 31a of the device 26. The proximal end of thread 52 is connected to a suitable finger actuatable member such as pull ring 57, illustrated in FIGS. 1 and 2, which can be pulled away from handle 32 to commence the unraveling of the crocheted material of mesh 51 in a manner described in U.S. Pat. No. 5,653,748. Such unraveling of the mesh causes the expandable stent 22 to commence disengaging from device 26 in the manner disclosed in the Ultraflex Article. Thread 52 is thus included within the releasing means of apparatus 21 which is operable from the proximal extremity of shaft 31.

A visual marker 61 capable of being seen under direct vision is secured to one or both of the distal extremity 31b of the shaft 31 and the stent 22 for facilitating placement of the stent in the body 24. Visual marker 61 can be of any suitable type and is preferably secured or otherwise coupled to the stent 22 or mesh 51 and preferably to the mesh 51. Apparatus 21 is preferably utilized with a scope 62 that is extendable into the body cavity 23 alongside the device 26 to permit direct visualization of the marker 61 within the cavity 23. As illustrated in FIG. 2, scope 62 has a distal face 63 providing a field of view to the operator so as to permit such visualization of the marker 61. In addition, the scope is preferably coupleable to a light source and includes an optical fiber for illuminating the field of view.

In the embodiment of apparatus 21 shown in FIGS. 1-9, the visual marker 61 is in the form of a colored band 66 extending around mesh 51, which binds down stent 22 prior to the stent's deployment. Band 66 can be placed at any suitable position along the length of prosthesis 22 and can have a length, that is in the longitudinal direction of the stent 22, ranging from two to fourteen millimeters and preferably from nine to fourteen millimeters. The band 66 can be of any suitable color, such as black, blue, green, yellow, red or purple, which preferably contrasts with the color of the threaded mesh 51 and further preferably contrasts with the color of stent 22 and is easily seen under the light from scope 62. The colored band 66 can be made of any suitable material such as silicone or another polymer. Band 66 is preferably a tubular member that is more preferably single walled, and can be extruded from a Silastic material sold by Dow Corning Corporation of Midland, Mo. When such Silastic material is used, band 66 can be swelled in a suitable solvent such as Forane 141B, Heptane or HCFC and then slipped over the distal end of device 26 and stent 22 for placement at the desired position on the stent. Before contraction of the Silastic material of the band 66, the free end of thread 52 can be looped between the band 66 and stent 22 or between the band 66 and the mesh 51 before extending the thread 52 proximally through skive 56.

Band 66 is preferably placed a distance from one end 42 or 43 of the stent 22 equal to the length to which the stent shrinks, contracts or foreshortens when released from the device 26. In this regard, the wire mesh body 36 of stent 22 is moveable from a first or contracted position in which the stent has an expanded length and a reduced diameter, as shown in FIGS. 1-6, and a second or expanded position in which the stent has a reduced length and an expanded diameter, as shown in FIG. 9. As such, the stent 22 has a first or extended length when secured to the shaft 31, as shown in FIGS. 1-6, and a second or reduced length shorter than the first length when fully released from the device 26 and expanded against the wall of the cavity 23, as shown in FIG. 9. Actuation of pull ring 57 and the subsequent release of thread 52 from band 54 results in the outward expansion of wire mesh 36 and the simultaneous reduction in length of stent 22 in a wave-like or sequential manner along longitudinal axis 41 (see FIGS. 7-9). As discussed above, the release of stent 22 commences at its proximal end portion 22a, and thus stent 22 contracts distally in length during its release sequence. Colored band 66 is placed a distance from the distal end 22b of the contracted stent 22 equal to the length that the stent 22 will assume when fully released from device 26.

Radiopaque or other markers can be placed on device 26 and/or stent 22 to permit fluoroscopic visualization, in addition to the direct visualization through scope 62, of the markers and/or stent 22 during deployment. For example, radiopaque markers 67 can be provided on shaft 31 of the device 26.

In operation and use, distal extremity 31b of the shaft 31 of apparatus 21 is adapted for extending into the cavity 23 of the body 24. Proximal extremity 31a of the shaft is accessible from outside of the body 24 when the distal extremity 31b is disposed in the cavity 23. In one preferred method of using apparatus 21, scope 62 is advanced through mouth 27 and esophagus 28 to the vicinity of a stricture 71 having opposite first or proximal and second or distal margins 71a and 71b and formed by a cancerous or other growth 72 in the wall 29 of the esophagus 28 to locate the proximal and distal margins 71a and 71b of the stricture. In this step, the scope is advanced to the distal margin 71b and the depth of insertion from the patient's incisors recorded. The scope is then retracted to the proximal margin 71a and the position recorded. The difference of these two measurements is the length of the stricture. With the distal extremity of the scope 62 located at the proximal margin 71a of the stricture, the distal extremity of device 26 is then introduced (see FIGS. 1-9). As part of the method for introducing device 26 into body 24, a guide wire (not shown) can be first placed in the esophagus 28 and thereafter apparatus 21 advanced over the guide wire to the desired location. The guide wire is pulled from the proximal extremity of apparatus 21 leaving device 26 and stent 22 within the esophagus 28. The operator utilizes handle 32 of device 26 to move shaft distal extremity 31b and align visual marker 61 with the distal extremity of the scope 62 and thus the proximal margin 71a of stricture 71. The movement of visual marker 61 can be visualized by the operator by means of scope 62.

Figure 8:
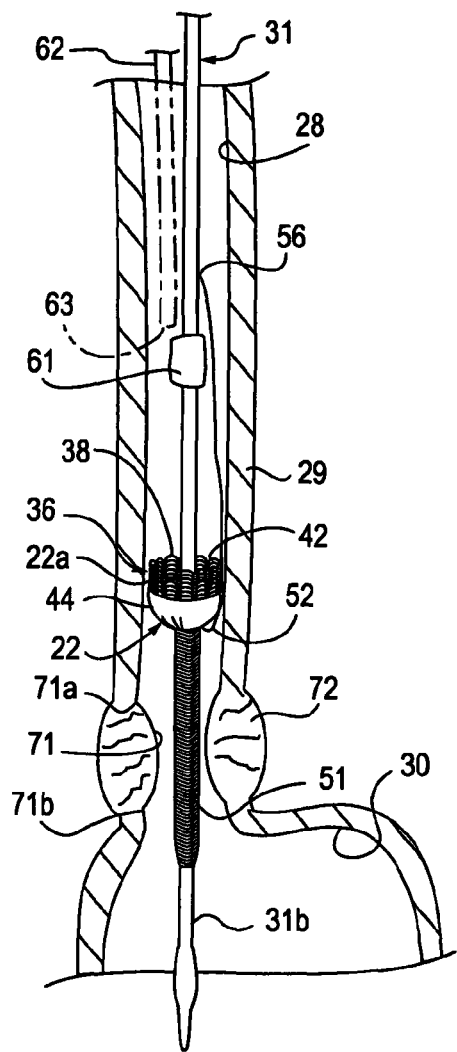
FIG. 8 is an enlarged elevational view, similar to FIG. 2, of the apparatus of FIG. 1 in a position similar to the fifth position of FIG. 7 in the passageway of the patient.

Once visual marker 61 has been so desirably aligned relative to the wall 29 forming esophagus 28, and the growth 72 formed in the wall 29, the distal extremity of scope 62 is retracted to a position proximal of stent 22 so as to be out of the way during stent deployment. For example, the distal extremity of the scope 62 can be retracted to skive 56. The operator pulls ring 57 to commence the removal of marker 61 from the bound down stent 22 and the subsequent deployment of the stent 22 from shaft distal extremity 3 1b. The pulling of ring 57 and thread 52 attached thereto causes colored band 66 to fold back on itself and roll proximally along the stent 22 after the band 66 is moved from its initial or home position of FIG. 3. FIG. 4 shows colored band 66 after it has been moved from its home position on the stent. In FIG. 5, the colored band 66 has been moved further proximally on stent 22 and is approaching the proximal end of wire mesh 51. FIG. 6 shows the colored band 66 after it has been pulled completely off mesh 51 and thread 52 has been released from securing band 54. In FIG. 7, the colored band 66 has moved further proximally on shaft 31 by the continued pulling of thread 52 and the proximal end portion of the crocheted mesh 51 has been released to permit expansion of the proximal end portion 22a of the stent 22. FIG. 8 shows stent 22 and device 26 within esophagus 28 after the stent has been further released from the position of FIG. 7. In FIG. 9, the stent 22 has been fully deployed and the distal end of thread 52 is shown free from the stent 22 and distal extremity 31b of shaft of 31. Membrane 44 and the base of proximal end portion or flare 22a and distal end portion 22b are shown covering the stricture 71. The expanded stent 22 forces the wall 29 of esophagus 28 outwardly at stricture 71 so as to increase the size of the opening or passageway of the esophagus 28 at stricture 71 and thus enhance flow through the growth 72.

Once expandable stent 22 has been fully deployed within esophagus 28, device 26 is pulled upwardly through the stent 22 and out of esophagus 28. Colored band 66 is appropriately sized so as to remain on shaft 31 during the removal of device 26 from human body 24.

As can be seen, visual marker 61 facilitates placement of the stent 22 within esophagus 28 by permitting the operator to longitudinally position the stent within the esophagus 28 at a position which anticipates the foreshortening of the stent during deployment. When the stent is deployed from its proximal end, for example, marker 61 permits the operator to predict where the proximal end 42 of the stent will rest on the esophageal wall 29 after the stent has been deployed and can thus make proper placement of the stent in the stricture 71 easier. Apparatus 21 allows placement of stent 22 without the need of fluoroscopy. As such, the patient and operator are not exposed to undesirable x-rays during the placement procedure. Apparatus 21 eliminates inaccuracies associated with stent placement relative to external markers, which can move during the procedure, by not requiring the use of such external markers. Savings in the cost of a stent placement apparatus may be achieved by apparatus 21. Further, stents 22 and other prostheses can be placed in outpatient surgery centers that do not have fluoroscopic equipment available.

Although stent 22 has been described and disclosed as being released from its proximal end portion 22a so as to expand in a distal direction, it should be appreciated that the stent can be released from its distal end portion 22b and expand in a proximal direction and be within the scope of the present invention. In this embodiment and procedure, the stent 22 contracts proximally in length during its release sequence. Colored band 66 would be placed a distance from the proximal end 22a of the contracted stent 22 equal to the length that the stent 22 will assume when fully released from device 26.

Figure 10:
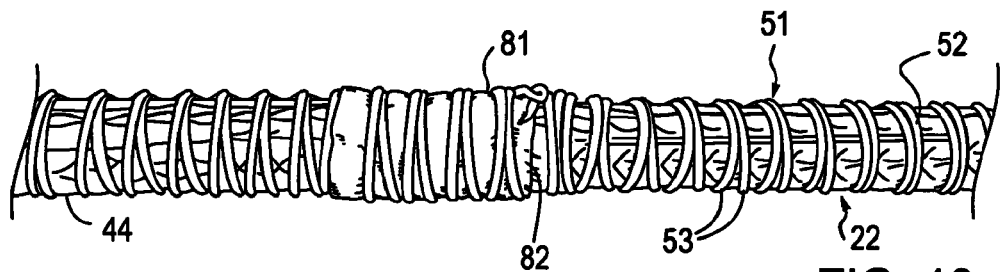
FIG. 10 is a side elevational view, similar to FIG. 3, of another embodiment of an apparatus for guiding deployment of an implantable prosthesis of the present invention.

The visual marker of the present invention can be broadly defined as any characteristic or feature included in the apparatus 21, whether on the prosthesis 22, device 26 and/or elsewhere on the apparatus 21, which can be observed under direct visualization so as to facilitate placement of the stent or other prosthesis within the mammalian body. Accordingly, other embodiments of the visual marker can be provided. For example, the visual marker of the present invention can be a colored marker 81 looped around thread 52 and bound to stent 22 by thread 52 (see FIG. 10). In one preferred embodiment, colored marker 81 is a flat piece of paper, polymer or other plastic having a fold 82 around thread 52, for example at one of loops 53 of the thread 52. Marker or flag 81 can have a size similar to the size of marker 61 and can extend around all or less than all of the circumference of the stent 22. The folded halves of colored marker 81, extending from fold 82, are secured together by any suitable means such as an adhesive. The colored marker 81 is then flattened against the outer cylindrical surface of stent 22 and such flattened portioned secured to the stent by other loops 53 of the thread 52 so as to be positioned under mesh 51.

The operation and use of apparatus 21 having colored marker 81 thereon is substantially similar to the operation of apparatus 21 discussed above. The colored marker 81 is removed from stent 22 by the unraveling of threaded mesh 51. Fold 82 serves to retain the colored marker 81 on thread 52 after the marker 81 is freed from stent 22. Colored marker 81 is pulled with thread 52 up to skive 56, which is smaller than the colored marker 81 and thus precludes the marker 81 from being pulled through device 26. As mesh 51 is further unraveled, thread 52 is pulled through fold 82. A knot or other suitable means is formed at the end of thread 52 for precluding the thread from being pulled through the colored marker 81. As a result, the colored marker 81 is removed from body 24 with the removal of device 26.

Figure 11:
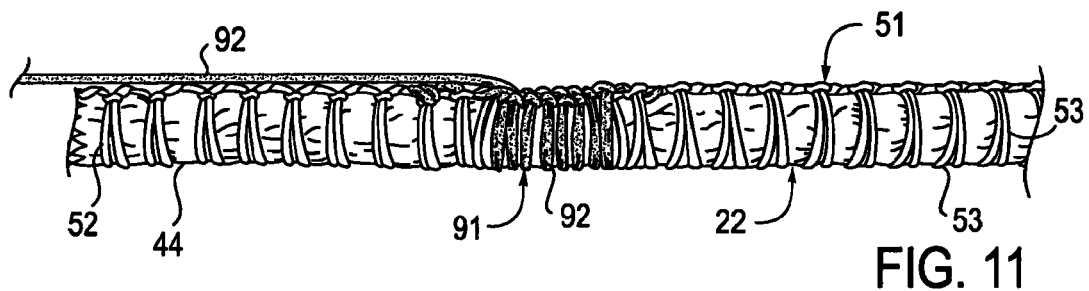
FIG. 11 is a side elevational view of a further embodiment of an apparatus for guiding deployment of an implantable prosthesis of the present invention.

In a further embodiment, visual marker 91 is formed by an additional thread 92 which is tightly wound around a portion of the stent 22 to form a plurality of closely spaced loops at the desired location of the marker. Visual marker 91 is illustrated in FIG. 11, where additional thread 92 has been colored so as to distinguish it from thread 52. Marker 91 can have a size similar to the size of marker 61. Additional thread 92 is preferably of a different color than thread 52 and stent 22, such as white or green, so as to be easily viewed by the operator looking through scope 62 of apparatus 21. In one preferred embodiment, a pair of adjacent loops 53 of threaded mesh 51 are spaced apart a sufficient distance, for example a distance ranging from two to twenty millimeters and preferably ranging from two to ten millimeters, so as to permit a sufficient length of the additional thread 92 to be tightly wound between the adjacent loops 53. One end of thread 92 is secured to threaded mesh 51 or device 26 any suitable means. For example, such end of thread 92 can be secured to shaft 31 proximal of the stent 22 by a band similar to band 54 or can be releaseably tied to or tucked under the thread 52 of mesh 51. The other end of the thread 92 extends proximally, for example along the thread 52, before entering skive 56 and traveling to proximal extremity 31a of shaft 31 and handle 32. The proximal end of the additional thread 92 can be wound within the shaft 31 to the thread 52 and, like the thread 52, can be secured to pull ring 57.

In operation and use, apparatus 21 having visual marker 92 thereon can be utilized in the manner discussed above with respect to markers 61 and 81. In a preferred method of operation, the operator pulls ring 57 to commence the simultaneous unraveling of thread 92 and thread 52. As a result of a difference in length of threads 52 and 92, that is the length of thread 52 from ring 57 to the proximal loop 53 adjacent visual marker 91 is greater than the length of thread 92 from ring 57 to visual marker 91, the marker 91 unravels before the portion of threaded mesh 51 in the vicinity of marker 91 unravels so that the stent 22 is not released until after the visual marker 91 has been removed from the stent. Entanglement of thread 52 with thread 92 in the vicinity of visual marker 91 is thus minimized.

Figure 12:
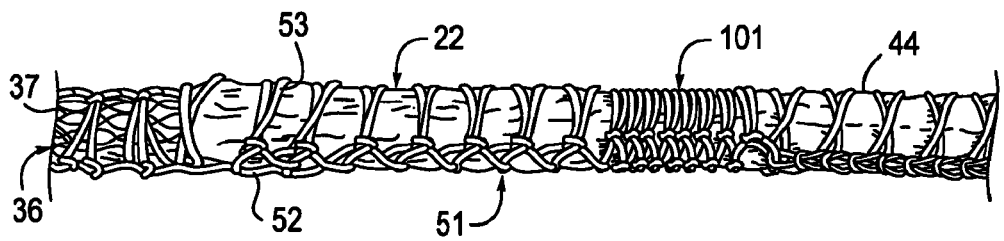
FIG. 12 is a side elevational view of yet another embodiment of an apparatus for guiding deployment of an implantable prosthesis of the present invention.

In a further embodiment, shown in FIG. 12, a portion of mesh 51 in the location where a visual marker is desired, is tightly spaced around stent 22 so as to create a densely spaced portion of the threaded mesh 51 which is visually distinct from the remainder of the mesh 51 by virtue of the tight or close spacing of successive loops. Such a visual marker 101 can be further distinguished from the remainder of threaded mesh 51 by applying a colored ink to such tightly wound portion of the mesh 51. Different printing methods can be used, for example pad printing, jet printing or straight painting, to apply the colored ink to the tightly wound portion of mesh 51 forming marker 101. The types of inks used include fluorescent dyes and inks approved for medical devices.

An apparatus 21 having visual marker 101 thereon can be utilized in the manner discussed above with respect to markers 61, 81 and 91. Visual marker 101 is removed from the stent 22 by unraveling threaded mesh 51 during the release of the stent.

Figure 13:
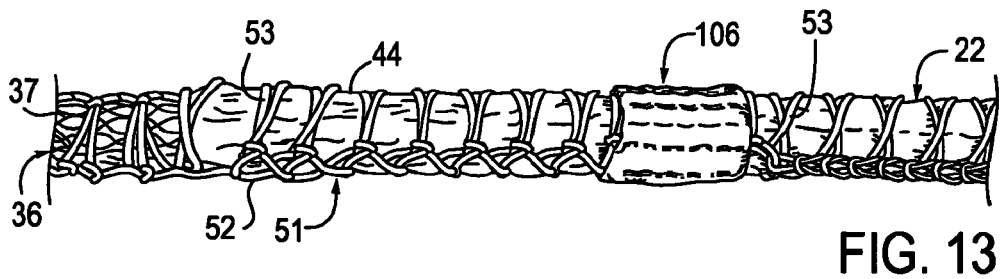
FIG. 13 is a side elevational view of yet a further embodiment of an apparatus for guiding deployment of an implantable prosthesis of the present invention.

In another embodiment, a visual marker 106 can be provided on stent 22 by applying a bioabsorbable material around the threaded mesh 51 and stent 22 at the desired location on the contracted stent. The bioabsorbable material of marker 106 can optionally be applied over one or more of the loops 53 of mesh 51 or merely in between adjacent loops 53. Although visual marker 106 is shown in FIG. 13 as being applied circumferentially around the stent 22, it should be appreciated that the material of visual marker 106 can be applied less then circumferentially around the stent 22 and/or as a plurality of longitudinally spaced-apart arcuate strips to form the visual marker. The bioabsorbable material forming the visual marker can be of any suitable type, for example a gelatin, and is preferably of a color that is different than the color of thread 52 and stent 22.

In operation of apparatus 21 having visual marker 106 thereon, once distal extremity 31b of shaft 31 and stent 22 thereon have been placed within cavity 23, the dissolving of the material of visual marker 106 commences. The dissolving rate is slow enough to allow the operator to visualize the marker 106 and desirably position the stent 22. In one preferred method of operating apparatus 21 with marker 106 thereon, the operator waits a sufficient period of time for marker 106 to dissolve before releasing threaded mesh 51 and permitting stent 22 to open in the cavity 23.

Radiopaque material can be included within the material of stent 22, such as membrane 44 thereof, and/or within the material of any of the visual markers hereof and, as discussed above, radiopaque markers can be placed elsewhere on device 26 and/or stent 22 to permit fluoroscopic visualization of the markers and/or stent 22 during deployment. In addition, any of the visual markers of the present invention can be provided with a colorant to enhance visualization.

In a further embodiment of the invention (not shown), a visible marker can be attached directly to device 26 or other delivery system beneath the stent or other prosthesis 22. Such an embodiment can be particularly advantageous when the stent or other prosthesis 22 permits visualization of such marker beneath the stent or prosthesis.

Although the visual markers of the present invention have been described for use with a stent deployed in the esophagus, such markers are equally suitable for use with any other implant, prosthesis or device that is placed, delivered or deployed under endoscopic or direct visualization. For example, the visual markers hereof can also be used with pulmonary and colonic stents, urethral stents, duodenal stents, any other stent that can be deployed under endoscopic or direct visualization, endoscopic devices and any crochet or other type of delivery system.

As can be seen from the foregoing, the visual markers of the present invention advantageously permit the placement of a prosthesis without the need of fluoroscopy. As a result, fluoroscopic equipment set up and film preparation can be eliminated and operator exposure to x-rays minimized. The visual marker facilitates accurate placement of the prosthesis. Where the prosthesis is a stent or other device that contracts in length during deployment, the visual marker can be utilized to anticipate such contraction in length.

What is claimed is:

1. An apparatus for use by an operator in a cavity of a mammalian body with a scope having a distal face providing a field of view comprising:
    a flexible elongate member having a distal extremity adapted for extending into the cavity and a proximal extremity accessible from outside of the mammalian body when the distal extremity is disposed in the cavity,
    an expandable prosthesis, means for releasably securing the prosthesis to the distal extremity of the flexible elongate member, wherein the means for releasably securing the stent comprises a colored mesh; and
    a visual marker in the form of a colored band extending around the colored mesh; wherein the visual marker is colored with a colorant to enhance visualization and is capable of being seen under direct vision within said cavity using said scope without the need of fluoroscopy; wherein the band is a tubular member, and wherein the color of the band contrasts with the color of the mesh.

2. The apparatus of claim 1 wherein the means for releasably securing includes releasing means operable from the proximal extremity of the flexible elongate member.

3. The apparatus of claim 1 wherein the means for releasably securing includes crocheted material extending along at least a portion of the length of the prosthesis.

4. The apparatus of claim 3 wherein the crocheted material includes a thread having a plurality of loops extending around the prosthesis.

5. The apparatus of claim 1 wherein the prosthesis is a stent.

6. The apparatus of claim 1 wherein the prosthesis has a first length when secured to the flexible elongate member and a second length different from the first length when released from the flexible elongate member.

7. The apparatus of claim 6 wherein the visual marker is secured to one of the distal extremity of the flexible elongate member and the prosthesis a distance from one of the first and second ends of the prosthesis equal to the second length to facilitate desired placement of the prosthesis in the cavity.

8. The apparatus of claim 7 wherein the prosthesis foreshortens during release from the flexible elongate member, the second length being shorter than the first length so as to reflect such foreshortening.

9. The apparatus of claim 1 wherein the means for releasably securing includes a thread for crocheting the prosthesis to the distal extremity of the flexible elongate member, the thread being secured to the colored band so that upon pulling the thread to release the prosthesis the colored band is pulled off the prosthesis and onto the flexible elongate member.

10. An apparatus according to claim 1, wherein said outer surface of said visual marker comprises silicone.

11. The apparatus of claim 1, wherein the means for releasably securing the prosthesis is of a color that is different than the color of the visual marker.

12. The apparatus of claim 1,
wherein the expandable prosthesis has a length, and wherein the means for releasably securing the prosthesis to the distal extremity of the flexible elongate member extends along substantially the entire length of the prosthesis in a repeating pattern.

13. The apparatus of claim 12 wherein the means for releasably securing includes crocheted material extending along at least a portion of the length of the prosthesis.

14. An apparatus according to claim 12, wherein said outer surface of said visual marker comprises silicone.

15. The apparatus of claim 12, wherein the means for releasably securing the prosthesis is of a color that is different than the color of the visual marker.

16. The apparatus of claim 1, wherein the
expandable prosthesis has first and second ends.

17. The apparatus of claim 16 wherein the expandable prosthesis has first and second ends, the visual marker overlying the prosthesis intermediate the first and second ends.

18. An apparatus according to claim 16, wherein said outer surface of said visual marker comprises silicone.

19. The apparatus of claim 16, wherein the means for releasably securing the prosthesis is of a color that is different than the color of the visual marker.

20. The apparatus of claim 1,
said visual marker overlying the prosthesis intermediate the first and second ends and being capable of being seen by the operator in the field of view secured to one of the distal extremity of the flexible elongate member and the prosthesis for facilitating placement of the prosthesis in the mammalian body.

21. An apparatus for use by an operator in a cavity of a mammalian body with a scope having a distal face providing a field of view comprising:
a flexible elongate member having a distal extremity adapted for extending into the cavity and a proximal extremity accessible from outside of the mammalian body when the distal extremity is disposed in the cavity,
an expandable prosthesis stent having first and second ends, means for releasably securing the prosthesis to the distal extremity of the flexible elongate member and
a visual marker capable of being seen by the operator in the field of view secured to the prosthesis for facilitating placement of the prosthesis in the mammalian body; wherein the visual marker is colored to enhance visualization and permits the placement of the prosthesis without the need of fluoroscopy and is capable of being freed from the prosthesis; wherein the band is a tubular member.

* * * * *